(12) United States Patent
Lee et al.

(10) Patent No.: US 8,420,598 B2
(45) Date of Patent: Apr. 16, 2013

(54) MONO MODIFIED EXENDIN WITH POLYETHYLENE GLYCOL OR ITS DERIVATIVES AND USES THEREOF

(75) Inventors: Kang Choon Lee, Seoul (KR); Chan Woong Park, Yongin-si (KR); Yu Seok Youn, Seoul (KR); Su Young Chae, Gwangju (KR)

(73) Assignee: B & L Delipharm Corp., Suwon, Gyeonggi-do (KR)

( * ) Notice: Subject to any disclaimer, the term of this patent is extended or adjusted under 35 U.S.C. 154(b) by 219 days.

(21) Appl. No.: 12/596,010

(22) PCT Filed: Apr. 20, 2007

(86) PCT No.: PCT/KR2007/001935
§ 371 (c)(1),
(2), (4) Date: Oct. 15, 2009

(87) PCT Pub. No.: WO2008/130066
PCT Pub. Date: Oct. 30, 2008

(65) Prior Publication Data
US 2010/0137558 A1 Jun. 3, 2010

(51) Int. Cl.
*A61K 38/00* (2006.01)
*C07K 14/605* (2006.01)
(52) U.S. Cl.
USPC .............. 514/7.2; 514/6.7; 514/6.8; 514/6.9; 530/308
(58) Field of Classification Search .................. None
See application file for complete search history.

(56) References Cited

U.S. PATENT DOCUMENTS 7,009,033 B2 * 3/2006 Varshney et al. ............. 528/421
2005/0107297 A1 * 5/2005 Holmes et al. ................. 514/12

FOREIGN PATENT DOCUMENTS

| WO | 00/66629 A1 | 11/2000 |
| WO | 2004/089280 A2 | 10/2004 |
| WO | 2006/074600 A1 | 7/2006 |

OTHER PUBLICATIONS

Baillon, 2001, Bioconjugate Chemistry, vol. 12, pp. 195-202.*

* cited by examiner

*Primary Examiner* — Robert Landsman
*Assistant Examiner* — Ian Dang
(74) *Attorney, Agent, or Firm* — Cheryl H. Agris (57) ABSTRACT

Disclosed herein are exendin singly modified with polyethylene glycole or a derivative thereof, a method for the preparation of the same, and uses thereof. Exendin modified at lysine (27) with polyethylene glycol shows biological activity similar to that of natural exendin, but is improved in half life. In addition, the modification position and the number of PEG or its derivative are restricted so as to minimize the side effects caused by a variety of combinations of such factors. The exendin is useful in the prevention and treatment of diseases caused by the over-secretion of insulin, or diseases caused due to a decrease in plasma glucose level, the inhibition of gastric or intestinal motility, the promotion of satiety, or the inhibition of food intake, especially diabetes, obesity and irritable colon syndrome.

9 Claims, 9 Drawing Sheets

MONO MODIFIED EXENDIN WITH POLYETHYLENE GLYCOL OR ITS DERIVATIVES AND USES THEREOF

CROSS-REFERENCE TO RELATED APPLICATIONS

This application is a 371 of PCT/KR2007/001935 filed on Apr. 20, 2007, the contents of each of which are incorporated herein by reference.

TECHNICAL FIELD

The present invention relates to an exendin which is modified singly with polyethylene glycol or a polyethylene glycol derivative, a method for the preparation of the modified exendin, and the use of the modified exendin.

BACKGROUND ART

Glucagon-like peptide-1 (hereinafter referred to as GLP-1) functions to induce various biological effects, including the stimulation of insulin secretion, the suppression of glucagon secretion, the promotion of satiety, the inhibition of gastric or intestinal motility, the augmentation of glucose use, and the induction of weight loss. Also, GLP-1 is known to have functions of preventing the degeneration of pancreatic cells caused by the progression of type II diabetes, that is, non-insulin dependent diabetes mellitus (NIDDM), and of promoting the growth of nascent-cells so as to recover insulin secretion. Particularly, the conspicuous feature of GLP-1 resides in the ability to stimulate insulin secretion without the concomitant induction of hypoglycemia, which is a major risk of insulin therapy or oral therapy for inducing an increase in insulin expression. In addition, none of the adverse events associated with the long-term administration of the hypoglycemic agent sulfonylurea, such as the apoptosis and necrosis of pancreatic β-cells, are found with GLP-1. Therefore, GLP-1 is regarded as very useful in the treatment of type II diabetes.

However, therapy with GLP-1 is restricted in utility not only because the activity of GLP-1 itself is insufficient, but also because two truncated, native GLP-1 molecules, GLP-1 (7-37)OH and GLP-1(7-36)NH$_2$, have very short plasma half lives. In detail, GLP-1 is one of the substrates of endogenous dipeptidyl peptidase-IV, being inactivated by the removal of the N-terminal histidine-alanine dipeptide moiety (aa 7 and 8), which is known to be a major cause of the short biological life span thereof (O'Harte et al., 2000).

There are many approaches to reduce the degradation of GLP-1 or to extend the plasma lifespan of GLP-1 while maintaining the biological activity thereof, including the use of DPP-IV inhibitors (P93/01, NVP-LAF237, NVP-DPP728, 815541A, 823093, MK-0431, etc.), and the use of ligands acting to GLP-1 receptors or GLP-1 derivatives (exendin, liraglutide, GLP-1/CJC-1131, etc.).

Exendins, first discovered by John Eng (U.S. Pat. No. 5,424,286), are a family of polypeptides capable of reducing the blood level of glucose. Exendin-4 has the following amino acid sequence, sharing partial homology (53%) with GLP-1 (7-36)NH$_2$ (Goke et al., 1993).

His1-Gly-Glu-Gly-The-Phe-The-Ser-Asp-Leu-Ser-

Lys12-Gln-Met-Glu-Glu-Glu-Ala-Val-Arg-Leu-Phe-

-continued
Ile-Glu-Trp-Leu-Lys27-Asn-Gly-Gly-Pro-Ser-Ser-

Gly-Ala-Pro-Pro-Pro-Ser-NH$_2$

Exendins are found in the venom of the beaded lizard and the gila monster: exendin-3 is extracted from the poison of the beaded lizard, *Heloderma horridum* and exendin-4 is present in the gila monster, *Heloderma suspectum*. Exendin-4 is different from exendin-3 only in amino acid position 2 and 3. In mammals, exendins are resistant to DPP-IV digestion so that their half life is longer than that of GLP-1, which is 2 min or less (Kieffer T J et al., 1995). In an in vivo test, exendins were found to have a half life of 2~4 hrs and reach a sufficient level in the blood upon two or three abdominal administrations per day (Fineman M S et al., 2003). In addition, it is known that exendin-4 functions to regulate gastrointestinal motility, decrease food intake and inhibit blood glucagon (U.S. Pat. Nos. 6,858,576, 6,956,026 and 6,872,700). With regard to the effect of exendin-4 on glycemic control, HbA$_{1c}$ levels, the amounts of hemoglobin bound to glucose in blood, were measured to decrease by 1% or less in both groups administered with exendin-4 alone and in combination with an anti-diabetic agent, such as sulfonylurea or metformin (Egan J M et al., 2003). Recently, the sale of synthetic exendin-4 under the brand name of Byetta has been approved by the FDA.

Polyethylene glycol (PEG), a polymer having the chemical structure of HO—(—CH$_2$CH$_2$O—)$_n$—H, is strongly hydrophilic, and thus it can increase the solubility of medicinal peptides when it is coupled therewith. PEG, when properly coupled with medicinal peptides, increases the molecular weight of the modified peptides to protect them from renal filtration, cells recognizing exogenous antigens, antibodies, and enzymatic degradation while their major biological functions, such as enzymatic activity and receptor binding are maintained. When its molecular weight falls within the range from 1,000 to 100,000, PEG can be properly coupled with peptides. PEG with a molecular weight of 1,000 or higher is known to have very low toxicity. PEG ranging in molecular weight from 1,000 to 6,000 is distributed throughout the body and metabolized in the kidneys. Particularly, PEG having about MW 40,000 is distributed in blood and the liver and the metabolism thereof is conducted in the liver.

Generally, when administered via parenteral routes, medicinally or pharmaceutically useful proteins may be antigenic in the body, for the most part, poor in water solubility and have a short retention time in the body. Approaches to overcome these shortcomings are under study. U.S. Pat. No. 4,179,337 teaches that when proteins or enzymes conjugated with PEG are used as therapeutics, they enjoy advantages from PEG, including a decrease in antigenicity and an increase in water solubility and in retention time. Since this patent was granted, many attempts have been made to couple biologically active proteins with polyethyleneglycol to overcome various shortcomings. For instance, ribonuclease and superoxide dismutase were coupled with PEG (Veronese et al., 1985) and when coupled with polymers including PEG, proteins were reported to show increased water solubility in U.S. Pat. Nos. 4,766,106 and 4,917,888. In addition, it was disclosed that recombinant proteins coupled with PEG or other polymers are decreased in antigenicity and increased in retention time in U.S. Pat. No. 4,902,502.

Despite such advantages, PEG limits the function of the proteins conjugated therewith. In detail, PEG is conjugated with a protein via a covalent bond to a lysine residue(s) of the protein. When the lysine residue is directly responsible for the activity of the protein, the protein conjugated with PEG cannot perform the biological function any more. Furthermore, because the bonding of PEG with lysine residues takes place randomly, many kinds of PEG-protein conjugates may result, making it complicated to separate the desired ones from the conjugate mixture.

There have been many attempts to conjugate GLP-1 or analogues thereof and exendin, which are therapeutically useful and have a short half life with PEG. PCT Publication No. 04/093823 reports that, when coupled with one or more polyethyleneglycol molecules, GLP-1 compounds or derivatives thereof were increased in half life and underwent degradation at low rates. The incorporation of one or two cysteine residues into specific amino acid residues of a peptide of interest provides one or two thiol groups, which then act as sites with which PEG or derivatives thereof (particularly, PEG-maleimide) can form a covalent bond so as to produce polyethyleneglycolated GLP-1 compounds. In an alternative, GLP-1, analogues or fragments thereof are covalently bonded to polyethylene glycol or polyethylene glycol derivatives at lysine residues or the carboxyl terminus to produce modified molecules which are extended in half life and decreased in degradation rate. In PCT Publication No. 04/093823, it was disclosed that PEG or derivatives thereof. Can form covalent bonds with cysteine resides at positions 26 and 34, lysine resides at positions 18, 22 and 26, or the carboxyl terminal residue of GLP-1 or analogues. It is also suggested that one peptide molecule may be conjugated with one to six PEG molecules, which preferably range in molecular weight from 20,000 to 40,000 daltons. The polyethylene-glycolated GLP-1 compounds prepared according to the method of PCT Publication No. 04/093823 were disclosed to have longer half lives and lower degradation rates in relation to natural GLP-1 or $Val_8$-GLP-1(7-37)OH, while retaining all or some of the biological activity of natural GLP-1.

U.S. Pat. No. 6,924,264 addresses novel modified exendin and exendin agonist analogs. The modified exendin-4 has three amino acid residues (N-terminal histidine, lysine 12 and 27) capable of being linked to PEG. The PEG used in U.S. Pat. No. 6,924,264 has a molecular weight ranging from 5000 to 12,000 daltons and can form covalent bonds with epsilon-amino groups of two lysine residues. In contrast to natural GLP-1, which undergoes primary proteolysis, the exendins increased in molecular weight are removed from plasma through renal filtration.

As described above, various approaches can produce exendins which are increased in lifespan and improved in efficiency in comparison with natural exendins. However, when two or more PEG molecules are covalently bonded to biologically active pepti des, such as GLP-1 or exendins, the resulting conjugates may show disadvantageous properties insufficient to be used as drug for example, may be decreased in stability and biological activity.

Leading to the present invention, the intensive and thorough research into an improvement in the pharmaceutical effect of exendin, conducted by the present inventors, resulted in the finding that the modification of exendin at a specific amino acid position with PEG or a derivative thereof produces PEG-exendin conjugates which are improved in retention time within the body without loss of the biological activity of natural exendin, and have exellent pharmacokinetic profiles and pharmaceutical effects, thereby decreasing in dose or administration number in comparison with natural exendin.

DISCLOSURE OF INVENTION

Technical Problem

It is an object of the present invention to provide exendin singly modified with polyethylene glycol or a derivative thereof.

It is another object of the present invention to provide a method for the preparation of the exendin singly modified with polyethylene glycol or a derivative thereof.

It is a further object of the present invention to provide uses of the exendin singly modified with polyethylene glycol or a derivative thereof.

Technical Solution

In accordance with an aspect thereof, the present invention provides exendin singly modified with polyethylene glycol or a derivative thereof.

In accordance with another aspect thereof, the present invention provides a method for preparing exendin singly modified with polyethylene glycol or a derivative thereof.

In accordance with a further aspect thereof, the present invention provides uses of exendin singly modified with polyethylene glycol or a derivative thereof.

Advantageous Effects

Exendin modified at lysine 27 with polyethylene glycol shows biological activity similar to that of natural exendin, but is improved in half life. Also, the modification position and the number of PEG or its derivative are restricted so as to minimize the side effects caused by a variety of combinations of such factors. The exendin is useful in the prevention and treatment of diseases caused by the over-secretion of insulin, or diseases caused due to a decrease in plasma glucose level, the inhibition of gastric or intestinal motility, the promotion of satiety, or the inhibition of food intake, especially diabetes, obesity and irritable colon syndrome.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

In accordance with an aspect thereof, the present invention is directed to exendins modified singly with PEG or PEG derivatives, or pharmaceutically acceptable salts thereof.

In an embodiment of this aspect, the modified exendins may be derived from natural or recombinant exendins. In any case, the exendins are preferably based on exendin-4.

In another embodiment, exendin-4 is preferably modified at position 27 with PEG or a PEG derivative. Exendin-4 has three sites which can be modified with PEG or PEG derivatives (N-terminal histidine, and lysine residues at positions 12 and 27). However, if modified at two or more sites with PEG or its derivatives, exendin-4 is decreased in stability and biological activity for the target molecule to such a degree that it prevents the resulting molecules from being applied to pharmaceutical uses.

In a further embodiment of the present invention, the PEG which can modify exendins may be a straight or a branched type. In the latter case, PEG may be structured to have two or more branches. Preferable is PEG having three branches.

In addition, the PEG or derivatives thereof in accordance with an embodiment of the present invention preferably range in molecular weight from 2 to 60 kDa, and more preferably from 20 to 45 kDa. If the molecular weight is below the lower limit, the modified exendin is not greatly increased in half life compared with natural exendin. On the other hand, when the molecular weight exceeds the upper limit, the modified exendin may show low stability and biological activity with regard to target molecules.

Examples of the polyethylene glycol derivatives used in the present invention include methoxypolyethylene glycol succinimidylpropionate, methoxypolyethylene glycol N-hydroxysuccinimide, methoxypolyethylene glycol propionaldehyde, methoxypolyethylene glycol maleimide, and multi-branched types thereof, but are not limited thereto. Preferable are methoxypolyethylene glycol succinimidylpropionate, methoxypolyethylene glycol N-hydroxysuccinimide, methoxypolyethylene glycol pro-pionaldehyde, bi-branched methoxypolyethylene glycol N-hydroxysuccinimide or tri-branched polyethyleneglycol represented by the following chemical formula 1.

Figure 1:
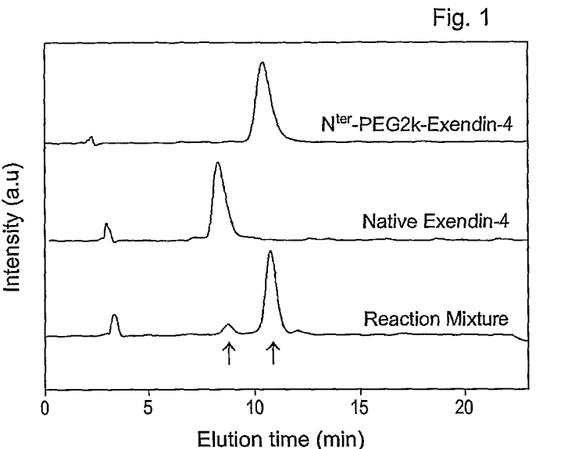
FIG. 1 is an HPLC chromatogram of the exendin-4 modified at the N-terminus with PEG and a reaction mixture after the N-terminal reaction.

Chemistry Figure 1

(wherein
n is an integer of 1 to 1,000, m is an integer of 10 to 1,000, the N-hydroxysuccinimide moiety is a functional group able to chemically react with proteins and peptides including exendins, and Z is $(CH_2)_S$ or $(CH_2)_S NHCO(CH_2)_S$, serving as a linker between exendin and polyethyleneglycol, wherein s is an integer of 1 to 6.)

In accordance with another aspect thereof, the present invention pertains to a method for preparing an exendin modified singly with the polyethyleneglycol or polyethyleneglycol derivative, comprising reacting polyethyleneglycol or a derivative thereof with exendin in the presence of a reducing agent in a solvent (step 1); storing the reaction mixture of step 1 at a predetermined temperature for a predetermined period of time in the dark (step 2); removing unreacted materials from the reaction mixture (step 3); and separating and purifying an exendin modified singly with polyethyleneglycol or its derivative from the reaction mixture free of unreacted materials (step 4).

In an embodiment of the present invention, the reaction molar ratio of polyethyleneglycol or a derivative thereof to exendin is preferably within the range of 1:1-4, depending on the kind of polyethyleneglycol or its derivative. For example, methoxypolyethylene glycol propionaldehyde is preferably used in an amount of 1 to 2 moles per mole of PEG or its derivative. In the case of methoxypolyethylene glycol succinimidyl propionate, its amount preferably ranges from 1 to 4 moles per mole of PEG or its derivative. The solvent used in step 1 may be PBS or an organic solvent. DMSO is preferable. The molar ratio may be selected depending on various factors, including the molecular structure and molecular weight of PEG or its derivative, pH, reaction temperature, and reaction time.

In step 1, a reducing agent is further used. Examples of the reducing agent include $NaCNBH_3$ or triethylamine, but are not limited thereto.

Further, no particular limitations are imposed on the buffer. It may be any one that is usually used in the art. The buffer may be selected to be appropriate for the reaction conditions for polyethylene glycol.

Like the reaction molar ratio, it is preferable that the storage temperature and time are properly controlled according to the kind of polyethylene glycol or its derivative. The modified exendin may be stored, for example, at 4° C. for 2 hours or at room temperature for a shorter period of time. This is relevant to the reactivity of polyethylene glycol or its derivative. During the storage, modification occurs. After a suitable period of time, the reaction can be terminated with glycine.

In another embodiment, the unreacted materials of step 3 can be removed through a typical method. For example, dialysis in a suitable buffer, such as PBS (phosphate buffered saline), may be used.

Further, the separation and purification of step 4 may be performed using size extrusion chromatography or reverse high performance liquid chromatography.

In accordance with a further aspect thereof, the present invention pertains to a pharmaceutical composition, comprising exendin-4, modified singly with PEG or its derivative as an active ingredient, for the treatment and prevention of diseases caused by the over-secretion of insulin, a decrease in plasma glucose level, the inhibition of gastric or intestinal motility, the promotion of satiety, or the inhibition of food intake.

In an embodiment of the present invention, exendin-4 can be increased in half life with the retention of natural biological activity through modification at a predetermined position, preferably at lysine 27, with polyethylene glycol or a derivative thereof. In addition, the modification position and the number of PEG or its derivative are restricted so as to minimize the side effects caused by a variety of combinations of such factors.

As a result, the exendin, modified singly with polyethylene glycol or a polyethylene glycol derivative, is useful in the prevention and treatment of diseases caused by the over-secretion of insulin, such as diabetes and obesity, and due to a decrease in plasma glucose level, the inhibition of gastric or intestinal motility, the promotion of satiety, or the inhibition of food intake, such as irritable colon syndrome.

The composition comprising PEG-modified exendin as an active ingredient in accordance with the present invention may be formulated into various oral or parenteral dosage forms.

For the formulation of the active ingredient, a diluent or an expedient, such as a filler, a thickener, a binder, a wetting agent, a disintegrant, a surfactant, etc., may be typically used. Examples of oral solid dosage forms include tablets, pills, powders, granules, and capsules. These solid forms are usually formulated with at least one expedient, such as starch, calcium carbonate, sucrose, lactose, or gelatin. In addition to the expedients, a lubricant, such as magnesium stearate or talc, may be used. Examples of oral dosage liquid forms include suspensions, liquids for internal use, emulsions, and syrups. These dosage forms may include various expedients, such as a wetting agent, a sweetener, a flavor, and/or a preservative, in addition to a simple diluent, such as liquid or liquid paraffin. Examples of parenteral dosage forms include sterile aqueous solutions, non-aqueous solvents, suspensions, emulsions, freeze-dried agents, and suppositories. As for non-aqueous solvents or suspensions, their examples include propylene glycol, PEG, vegetable oil, such as olive oil, and injectable ester such as ethyl oleate.

The dosage amount of the composition according to the present invention varies depending on various factors, including body weight, age, sex, body condition, diet, administration time, administration route, excretion rate, and disease severity. Generally, an effective amount may be completely used through several administrations over one or two weeks. Within an effective daily dosage, the composition of the present invention may be administered once, or in multiple doses per day.

A better understanding of the present invention may be obtained through the following examples which are set forth to illustrate, but are not to be construed as the limit of the present invention.

MODE FOR THE INVENTION

Example 1

Preparation of Methoxypolyethylene propionaldehyde Coupled Exendin-4

To 0.5 ml of exendin-4 (American Peptide, 1 mg/ml in 50 mM sodium acetate, pH 5.5) was added methoxypolyethylene propionaldehyde (Nektar, mPEG-propionaldehyde, mPEG-ALD, 2 kDa, 0.95 mg/ml in 50 mM sodium acetate, pH 5.5), followed by the addition of 20 mM $NaCNBH_3$ as a reducing agent. The molar ratio of mPEG-ALD to exendin-4 was 1:1-2. Reaction between mPEG-ALD and exendin-4 was conducted for 2 hours at 4° C. in the dark. The reaction was terminated with an 0.1% aqueous trifluoroacetic acid (TFA) to afford an exendin modified at the N-terminus with PEG.

Example 2

Preparation of Methoxypolyethylene Glycol Succinimidyl Propionate-Modified Exendin-4

Exendin-4 (American Peptide, in DMSO) was mixed with an equal volume of 2, 5, 10, or 20 kDa methoxypolyethylene glycol succinimidyl propionate (Nektar, mPEG-succinimidyl propionate (mPEG-SPA) in DMSO). Also, an equal volume of 9% tri-ethylamine (TEA in DMSO) was added as a reducing agent in an amount that formed a final concentration of 3%. The resulting mixture was allowed to react for about 60 min at room temperature in the dark. The molar ratio of exendin-4 to mPEG-SPA was 1-4:1. The reaction was terminated by adding a 0.1% TFA solution in distilled water at an equal volume to the reaction mixture to produce exendin-4 modified with 2, 5, 10 or 20 kDa PEG-modified exendin-4 (respectively, PEG2K-exendin-4, PEG5K-exendin-4, PEG10K-exendin-4 and PEG20K-exendin-4).

Example 3

Preparation of Straight, Bi-Branched or Tri-Branched PEG-modified Exendin-4

Exendin modified at the N-terminus with PEG was prepared in a manner similar to that of Example 2, with the exception that straight (20 kDa), bi-branched (20 kDa) or tri-branched (23 or 40 kDa) methoxypolyethylene glycol N-hydroxysuccinimide (Nektar) was used.

Experimental Example 1

Separation, Purification and Identification of Position Isomer of Exendin-4 Modified Singly with PEG In order to separate PEG-modified exendin-4, an experiment was carried out as follows.

Figure 2:
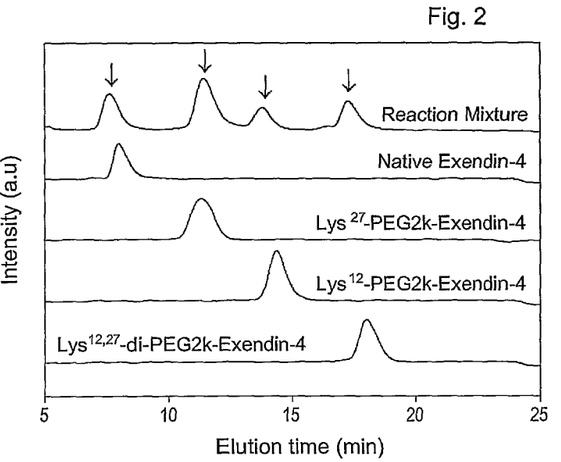
FIG. 2 is an HPLC chromatogram of the products resulting from the reaction of PEG with lysine residues of exendin-4.
Figure 3:
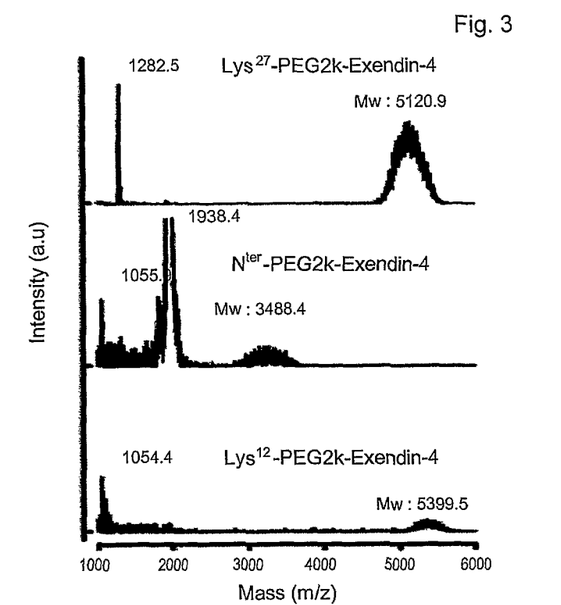
FIG. 3 shows MALDI-TOF mass spactra of the exendin-4 conjugates digested with lysine-C.

The PEG-modified exendin-4 prepared in Examples 1~3 were separated by column chromatography using a Lichrospher RP-8 column (250×4.0 mm, 5 μm, Merk, Germany) with a mixture of a 0.1% TFA solution in acetonitrile and a 0.1% TFA solution in distilled water serving as a mobile phase. The mobile phase consisted of 35-45% of solvent B (acetonitrile containing 0.1% TFA) and 55-65% of solvent A (0.1% distilled water containing 0.1% TFA), and solvent A and solvent B were linearly changed. The exendin-4 eluted from the column chromatography was quantitatively analyzed by reading peaks at 215 nm with a UV spectrophotometer. In order to examine the number of the PEG conjugated to exendin-4, the PEG-modified exendin-4 separated through column chromatography was subjected to mass analysis using MALDI-TOF (Matrix assisted laser desorption/ionization time-of-flight) mass spectrometry. Each position isomer was digested with lysine-C endopeptidase before MALDI-TOF mass spectrometry. Each PEG conjugate was dissolved at a concentration of 1 mg/ml in 50 μl of triethylamine-HCl buffer (10 mmol/l; pH 7.4) to which 50 μl of the enzyme (1 mg/ml) was added, followed by enzymatic digestion at 37° C. for 1 hour. 5 μl of 10% (v/v) TFA was added to terminate the digestion of lysine-C, and the digests were analyzed using MALDI-TOF mass spectrometry. The results are shown in FIGS. 1 to 3 and Table 1.

TABLE 1

| Position of PEG Modification | Calculated weight | | Measured in MALDI-TOF | |
| --- | --- | --- | --- | --- |
| | Exendin-4 Mass | PEG Mass | Exendin-4 Mass | PEG Mass |
| Lys-27 | 1278.3 | 5127.4 | 1282.5 | 5120.5 |
| N-terminus | 1921.2, 1024.1 | 3478.3 | 1988.4, 1055.9 | 3488.4 |
| Lys-12 | 1024.1 | 5381.5 | 1064.4 | 5399.5 |

FIG. 1 is an HPLC chromatogram of the exendin modified at the N-terminus with PEG. As can be seen in the chromatogram, the reaction mixture was separated into two different materials which were identified as unreacted exendin-4 and N-terminally PEG modified exendin-4, respectively. In addition, the N-terminally PEG modified exendin-4 was measured to be 98% or higher in purity.

FIG. 2 is an HPLC chromatogram of the products resulting from the reaction of PEG with lysine residues of exendin-4. As seen in this chromatogram, the reaction mixture of Examples 2 and 3 was composed of four different materials. As can be seen in FIG. 3 and Table 1, these four materials were analyzed to be unreacted natural exendin-4, exendin-4 modified at lysine-27 with PEG ($Lys^{27}$-PEG2k-exendin-4), exendin-4 modified at lysine-12 with PEG ($Lys^{12}$-PEG2k-exendin-4), and exendin-4 modified at lysine-12 and 27 with PEG ($Lys^{12,27}$-PEG2k-exendin-4). The products finally obtained had a purity of 98% or higher.

Figure 4:
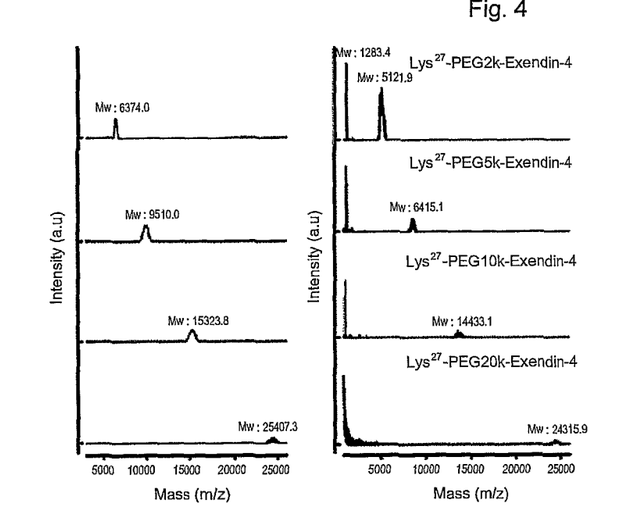
FIG. 4 shows MALDI-TOF spectra of the exendin-4 modified singly at lysine-27 with PEG, prepared in Example 2.

FIG. 4 shows MALDI-TOF spectra of the exendin-4 modified singly at lysine-27 with PEG in accordance with the present invention. In Example 2, PEG-exendin-4 conjugates having various molecular weights were produced as various molecular weights of PEG were used.

Experimental Example 2

Biological Activity of PEG-Exendin-4 Conjugates According to Position of PEG Modification In order to examine the biological activities of natural exendin-4 and PEG-modified exendin-4, experiments were carried out as follows.

Experimental Example 2-1

Assay for Promoting Insulin Secretion

Cells used for this assay were pancreatic islet cells of Sprague Dawley rats, which could be isolated by collagenase digestion and then Ficoll gradient centrifugation. After being cultured for 2~3 days in an incubator, the isolated pancreatic islet cells were suspended in 1 ml of KRH buffer (16.7 mM glucose) at a density of 20 cells per well into 24-well plates. Afterwards, natural exendin and exendin-4 isomers modified at the N-terminus, lysine-12 and lysine-27 with PEG ($N^{ter}$-PEG2k-exendin-4, $Lys^{12}$-PEG2k-exendin-4, and $Lys^{27}$-PEG2k-exendin-4) were added at a concentration of 0.1, 1, 10, and 100 nM to each well, respectively, followed by incubation for 2 hours. Then, 2001 of the culture was taken from each well and analyzed for insulin level using an insulin ELISA kit. The results are shown in FIG. 5.

Figure 5:
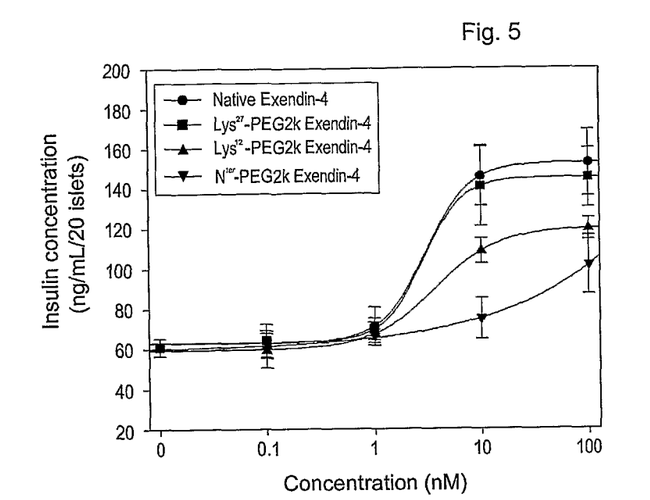
FIG. 5 shows insulin secretory capacities of natural exendin-4 and PEG-modified exendin-4.

As seen in FIG. 5, the insulin secretory capacity of $Lys^{27}$-PEG2k-exendin-4 was superior to that of the other modified exendin-4, and similar to that of natural exendin-4. $N^{ter}$-PEG2k-exendin-4 and $Lys^{12}$-PEG2k-exendin-4 were measured to show low insulin secretory capacity, with $N^{ter}$-PEG2k-exendin-4 being poorer. In addition, natural exendin-4, $Lys^{27}$-PEG2k-exendin-4, $Lys^{12}$-PEG2k-exendin-4 and $N^{ter}$-PEG2k-exendin-4 were found to have $EC_{50}$ values of 2.94, 3.11, 9.65 and 135.5 nM, respectively.

Experimental Example 2-2

Assay for Receptor Binding

In order to examine the interaction between the ligands exendin-4 and PEG-modified exendin-4 and the GLP-1 receptor, experiments were carried out as follows.

The insulin secretory cell line INS-1 was plated at a density of 2.5 $10^5$ cells per well onto 12-well plates and allowed to stably adhere to the bottom of the plates through incubation for about 2 days. After cell adhesion, the culture medium was substituted with a binding buffer to which $^{125}$I-exendin-4 (an exendin derivative stretching from amino acid residue 9 to amino acid residue 39) was then added in such an amount as to form a final concentration of 30 μM. Thereafter, natural exendin-4, $Lys^{27}$-PEG2k-exendin-4, $Lys^{12}$-PEG2k-exendin-4 and $N^{ter}$-PEG2k-exendin-4 were individually added in such an amount as to form a final concentration of 0.001~1000 nM, followed by allowing them to competitively bind to the receptor for 2 hours at room temperature. Cells were washed three times with cold PBS to remove unbound $^{125}$I-exendin-4. Finally, cells were disrupted with lysis buffer and measured for cell-bound exendin-4 level using a gamma counter. The results are shown in FIG. 6.

Figure 6:
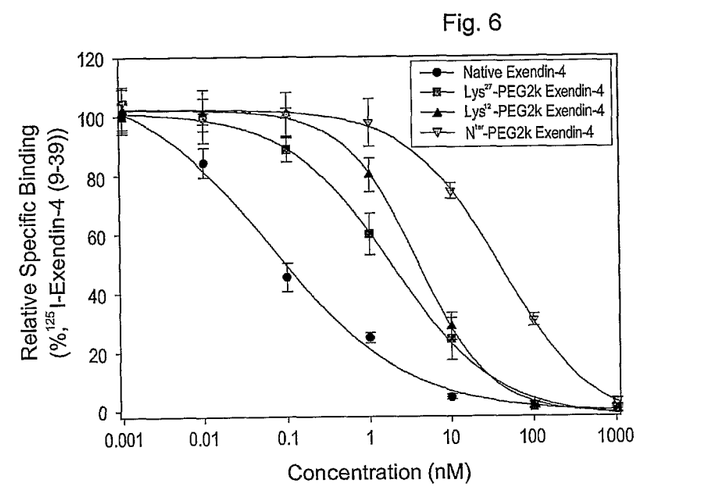
FIG. 6 shows binding behaviors of natural exendin-4 and PEG-modified exendin-4 to the GLP-1 receptor located on insulin secreting cell surfaces.

As seen in FIG. 6, the competitive binding of $^{125}$I-exendin-4 was decreased as the sample increased in concentration. In addition, the position isomers varied in binding intensity, depending on modification position. Natural exendin-4, $Lys^{27}$-PEG2k-exendin-4, $Lys^{12}$-PEG2k-exendin-4 and $N^{ter}$-PEG2k-exendin-4 were found to have an $IC_{50}$ value of 0.1, 1.8, 3.9 and 36.5 nM (concentrations when 50% $^{125}$I-exendin-4 was bound), respectively.

As apparent from these data obtained through cell culture and receptor binding assay, the PEG-modified exendin-4 isomers were found to be superior in biological effect and efficiency in the following order: $Lys^{27}$-PEG2k-exendin-4>$Lys^{12}$-PEG2k-exendin-4>$N^{ter}$-PEG2k-exendin-4.

Experimental Example 2-3

Animal Model Test

In order to examine the activity of natural exendin-4 and PEG conjugates in animal models, saline (control), natural exendin-4, and PEG-modified exendin-4 ($Lys^{27}$-PEG2k-exendin-4, $Lys^{12}$-PEG2k-exendin-4 and $N^{ter}$-PEG2k-exendin-4) were subcutaneously injected in a dose of 1 nmol/kg (dosage volume 100 l) into 6-week-old, male db/db mice (model mice suffering from diabetes)(C57/BLKS/J-db/db, Korea Research Institute of Bioscience and Biotechnology) 30 min before oral administration with 200 mg/ml of glucose (dosage volume 2001). 30 min before, at the time of, and 15, 30, 60, 120 and 180 min after the oral administration of glucose, blood samples were taken from the tail vein and monitored for glucose level. The results are shown in FIGS. 7 and 8.

Figure 7:
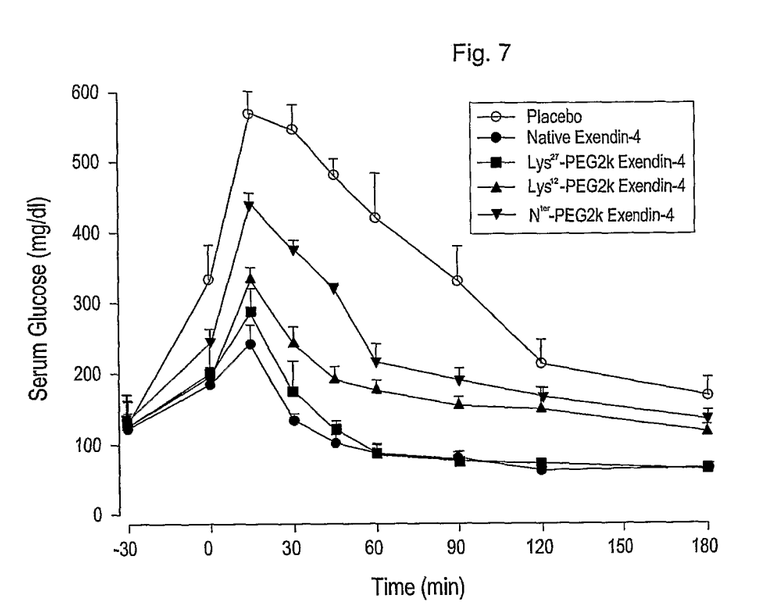
FIG. 7 shows glucose tolerance measured in animal models administered with the exendin-4 modified singly at different positions with PEG.

In the control, which was injected only with saline, as seen in FIG. 7, the blood glucose level increased sharply upon glucose administration and then decreased slowly. In contrast, the groups injected with natural exendin-4 and PEG-modified exendin-4 underwent a relatively slow increase in blood glucose level and a relatively rapid decrease in blood glucose level. Also, there are notable differences in blood glucose level between the groups administered with natural exendin-4 and PEG-modified exendin-4, which are believed to result from the fact that there are differences in activity and receptor binding ability between the PEG conjugates. Areas under the glucose curve plotted from 0 to 180 min on the basis of the result of FIG. 7 are shown in FIG. 8.

Figure 8:
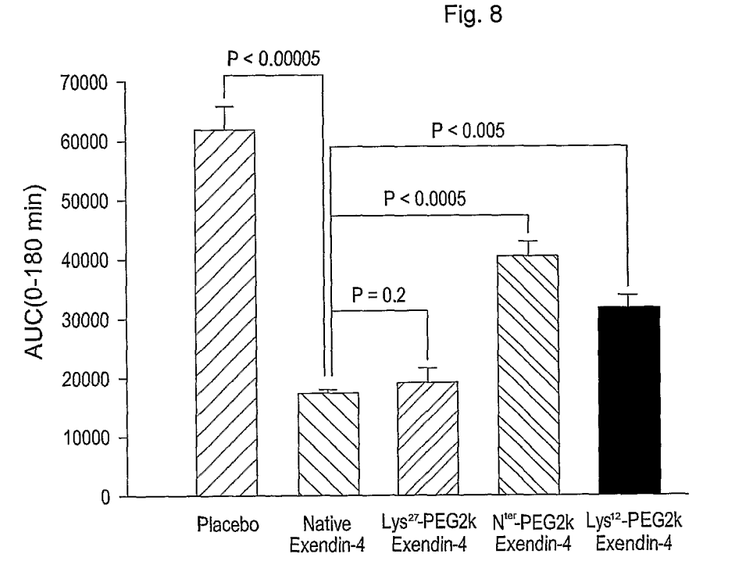
FIG. 8 shows areas under the glucose curve plotted from 0 to 180 min on the basis of the result of FIG. 7.

As seen in FIG. 8, Lys$^{27}$-PEG2k-exendin-4 was observed to have activity similar to that of natural exendin-4. Lys$^{12}$-PEG2k-exendin-4 and N$^{ter}$-PEG2k-exendin-4 showed low effects. This difference is believed to be attributed to the fact that there is a difference in biological activity among them.

Accordingly, the data obtained in the biological activity and animal model test of Experimental Example 2 demonstrate that the PEG conjugate with a PEG molecule linked to lysine 27 can decrease blood glucose levels at higher efficiency than can the other PEG conjugates.

Experimental Example 3

Analysis of Exendin-4 Modified Singly at Lysine-27 with PEG for Biological Activity According to Molecular Weight of PEG In order to examine the biological activity of the exendin-4, which was modified at lysine-27 with PEG in a manner similar to that of Experimental Example 1, according to the molecular weight of PEG, the following experiments were carried out.

Experimental Example 3-1

Promotion of Insulin Secretion

The same procedure as in Experimental Example 1-1 was conducted, with the exception that the exendin-4 modified with 2, 5, 10 and 20 kDa PEG-modified exendin-4 prepared in Example 2 (PEG2K-exendin-4, PEG5K-exendin-4, PEG10K-exendin-4 and PEG20K-exendin-4) were administered at a dose of 10 nM to rat pancreatic islet cells isolated from rats. The results are shown in FIG. 9.

Figure 9:
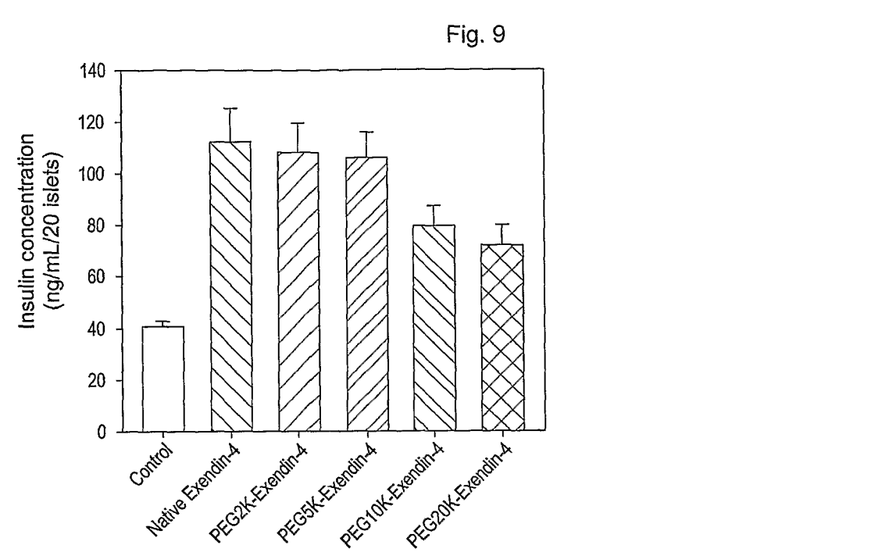
FIG. 9 shows the results of an assay of PEG-modified exendin-4 for insulin secretory capacity according to the molecular weight of PEG.

As shown in FIG. 9, the exendin-4 modified with PEG having a molecular weight of 5 kDa or less was not substantially different in biological activity from natural exendin-4. In contrast, the conjugates were observed to gradually decrease in biological activity with an increase in the molecular weight of the PEG. When modified with 20 kDa PEG, exendin-4 was measured to show 40% or higher of residual activity.

Experimental Example 3-2

Assay for Receptor Binding

A procedure similar to that of Experimental Example 1-2 was conducted, with the exception that the PEG conjugates, PEG2K-Ex-4, PEG5K-Ex-4, PEG10K-Ex-4 and PEG20K-Ex-4, prepared in Example 2, were administered at a dose of 0.001-1000 nM to the insulin secretory cell line INS-1. The results are shown in FIG. 10.

Figure 10:
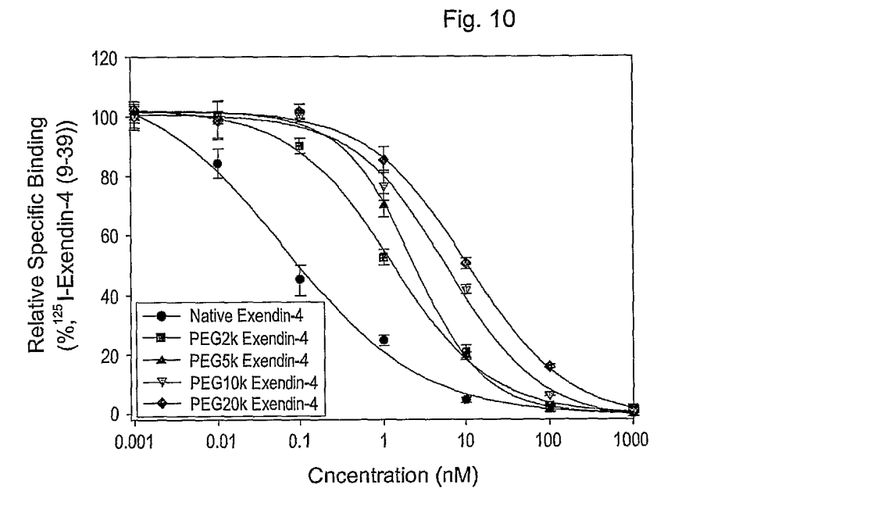
FIG. 10 shows the results of an assay of PEG-modified exendin-4 for binding to GLP-1 receptor according to the molecular weight of PEG.

It is apparent from the data of FIG. 10 that the modified exendin-4 decreases in receptor binding capacity as the PEG increases in molecular weight. Exendin-4 and PEG-modified exendin-4 were measured to have IC$_{50}$ values of 0.1 nM (natural exendin-4), 1.8 nM (PEG2k-exendin-4), 2.4 nM (PEG5k-exendin-4), 5.6 nM (PEG10k-exendin-4) and 10.7 nM (PEG20k-exendin-4). Hence, it is revealed through this experiment that the interaction between the PEG modified exendin-4 and the receptor becomes weak as the PEG increases in molecular weight, which incurs a decrease in the biological activity of exendin-4, that is, insulin secretory capacity. When modified at lysine-27, even with 20 kDa PEG (IC$_{50}$=10.7 nM), the exendin-4 was found to show higher receptor binding capacity than was the exendin modified at the N-terminus with low molecular weight PEG (IC$_{50}$=36.5 nM), as is apparent from the data of FIG. 6, obtained using exendin-4 modified with 2 kDa PEG.

Consequently, when modified at lysine-27, the PEG-modified exendin-4 retains the biological activity thereof even though the PEG has a large molecular weight.

Experimental Example 3-3

Measurement of Anti-Diabetic Activity in Animals

In order to examine the activity of natural exendin-4 and PEG-modified exendin-4 in animal models, saline (control), natural exendin-4, and the modified exendin-4 conjugates PEG2K-Ex-4, PEG5K-Ex-4, PEG10K-Ex-4 and PEG20K-Ex-4 prepared in Example 2 were subcutaneously injected into male db/db mice (mean blood glucose level 250 mg/dL) which were 6~7 weeks old (C57/BLKS/J-db/db, Korea Research Institute of Bioscience and Biotechnology), followed by monitoring levels in the blood taken from the tail vein. The results are shown in FIG. 11.

Figure 11:
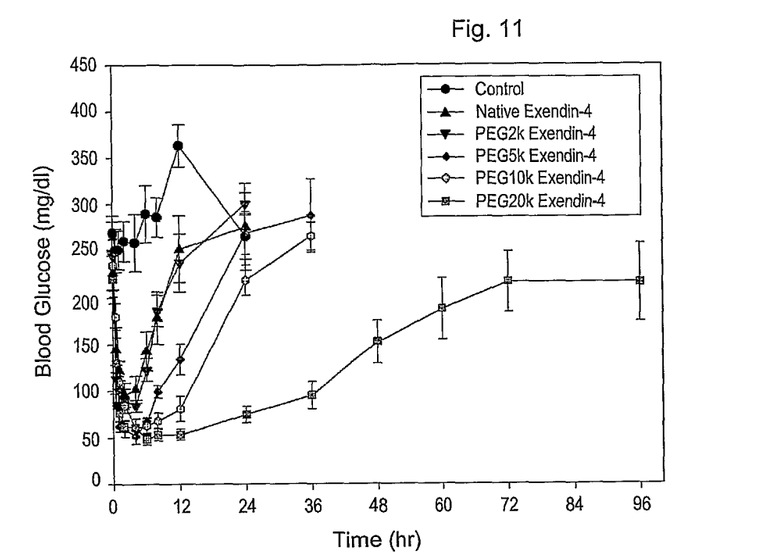
FIG. 11 shows changes in the blood glucose level of test animals administered with exendin-4 modified with PEG having different molecular weights.

As seen in FIG. 11, when injected into experimental animals afflicted with diabetes, exendin-4 and PEG-modified exendin-4 acted to induce insulin secretion in the body to sharply decrease plasma glucose to normal levels (<150 mg/dL). The control (injected with saline) continued to have high blood glucose levels. Natural exendin-4 and PEG-modified exendin-4 were shown to differ from each other in the retention period of normal blood glucose level. There is no substantial difference in blood glucose level-decreasing behavior between exendin-4 and PEG-modified exendin. In both the groups administered respectively with exendin-4 and PEG2k-exendin-4, blood glucose was maintained at normal levels until about 6 hours after the injection, and then returned to high levels. The exendin-4 modified with PEG5k or PEG10k showed a behavior of decreasing blood glucose levels at higher efficiency than did natural exenden-4, and was observed to keep blood glucose at normal levels for 12 and 18 hours, respectively. A significantly different behavior of decreasing blood glucose levels was detected in PEG20k-exendin-4, in which 20 kDa PEG was coupled. When administered at the same dosage, PEG20k-exendin-4 was shown to keep the normal blood glucose level for about 36 hours, which is twice that of PEG10k-exendin-4 and six times that of natural exendin-4. Thus, the exendin-4, modified at lysine 27 with a high molecular weight PEG, can be used as a long-acting anti-diabetic drug the medicinal efficacy of which can last for a prolonged period of time.

Experimental Example 3-4

Pharmacokinetic Behavior in Animal

As demonstrated in the above-described experiment, the exendin-4 modified at lysine-27 with a high molecular weight PEG showed the properties of a long-acting peptide drug. In order to examine the long-acting properties, exendin-4, PEG2k-exendin-4 and PEG20k-exendin-4 were observed for pharmacokinetic behavior.

SD rats weighing 200 g were subcutaneously injected with samples at a dose of 1 nmol/rat (4.18 μg/rat), followed by sampling blood through a tube inserted into the jugular vein. The blood samples were monitored for drug level using an ELISA kit. The results are given in FIG. 12.

Figure 12:
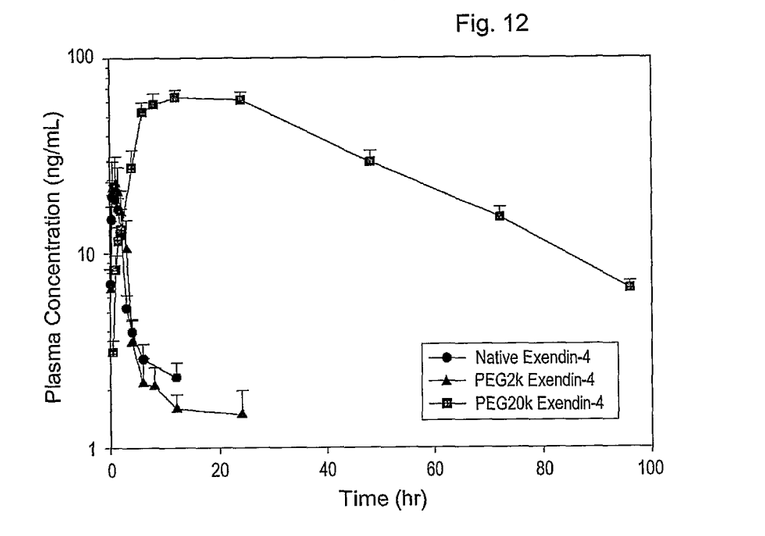
FIG. 12 shows changes in the blood glucose level of test animals subcutaneously administered with natural exendin-4, PEG2k-exendin-4 and PEG20k-exendin-4.

As is apparent from the data of FIG. 12, natural exendin-4 and PEG2k-exendin-4 showed similar pharmacokinetic behaviors, in which the blood level peaked 30-45 min after administration, then sharply decreased within a short period of time, and reached a basal line (<2 ng/mL) 4 hours after administration. Using this blood concentration plot, exendin-4 and PEG2k-exendin-4 were calculated to have an elimination half life of 1.6 0.4 and 1.5 0.3 hours, respectively. In contrast, when PEG20k-exendin-4 was injected, its blood level was observed to gradually increase and peak about 12 hours after injection, before slow reduction. The elimination half life of PEG20k-exendin-4 was calculated to be 22.0±1.7 hours.

Accordingly, the property of long-acting medicinal effect of PEG20k-exendin-4 is based on the pharmacokinetic behavior thereof, especially the long elimination half life.

Experimental Example 4

Analysis of Exendin-4 Modified Singly at Lysine-27 with PEG for Biological Activity According to Molecular Structure of PEG Through the experiments of Experimental Examples 1-3, the exendin-4 modified at lysine-27 with 20 kDa or higher molecular weight PEG was observed to exhibit the properties of a long-acting drug. Subsequently, in order to examine the influence of the molecular structure of the PEG on the efficacy and effect of the drug PEG molecules having different structures were linked to lysine-27 of exendin-4, and the resulting conjugates were analyzed for biological activity.

Experimental Example 4-1

Assay for Receptor Binding

Receptor binding capacity was measured in the same manner as in Experimental Example 2-1, with the exception that the cells were treated with exendin-4 modified with bi-branched PEG (20 kDa) and tri-branched PEG (23 kDa) prepared according to Example 3. The results are shown in FIG. 13.

Figure 13:
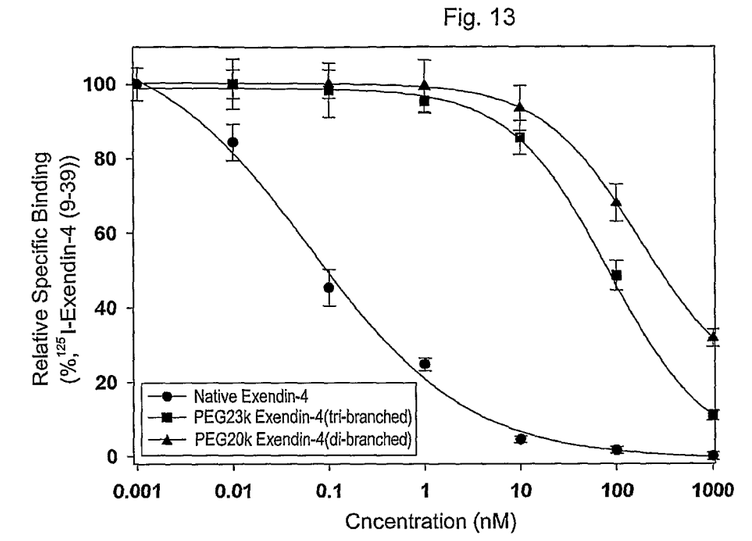
FIG. 13 shows the binding affinity of exendin-4 modified with two different PEG molecules, each having a mean molecular weight of 20000 daltons, for the receptor of insulin secretory cells.

As seen in FIG. 13, the binding capacity of PEG-modified exendin-4 was measured to be higher when using tri-branched PEG than when using bi-branched PEG. The PEG conjugates were calculated to have $IC_{50}$ values of 80.6 nM (tri-branched) and 280.8 nM (bi-branched), respectively.

Experimental Example 4-2

Measurement of Anti-Diabetic Activity in Animal

The same procedure as in Experimental Example 3-3 was repeated, with the exception that the cells were treated with exendin-4 modified with bi-branched PEG and tri-branched PEG prepared according to Example 3. The results are shown in FIG. 14.

Figure 14:
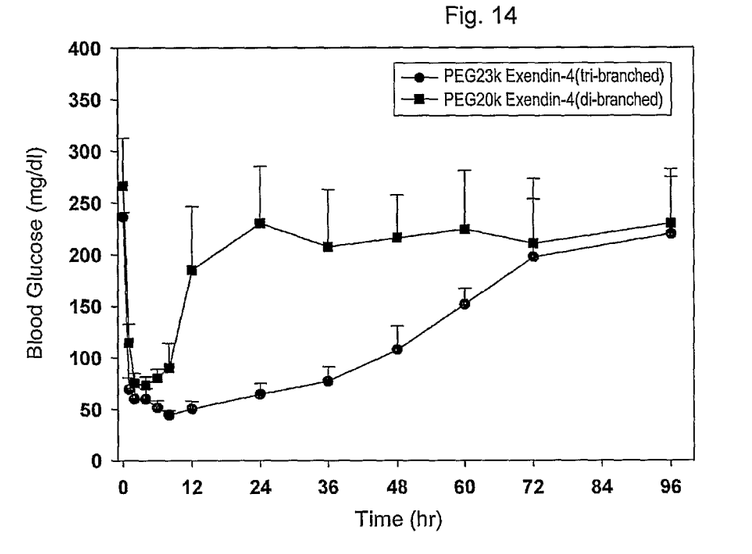
FIG. 14 shows anti-diabetic activity of exendin-4 singly modified with PEG of different molecular structures in test animals.

As can be seen in FIG. 14, when injected with the bi-branched PEG conjugate, the animals maintained blood glucose at normal levels until about 8 hours after the injection, and then returned to high levels. This is believed to be attributable to the fact that the bi-branched PEG conjugate has very low receptor binding capacity ($IC_{50}$=280 nM, refer to FIG. 13). In contrast, all of the tri-branched PEG conjugates showed an effect of decreasing blood glucose levels over 48 hours and thus can be used as long-acting drugs. The efficacy of tri-branched PEG conjugates is based on the pharmacokinetic behavior thereof, especially the elimination rate and distribution thereof.

Therefore, tri-branched PEG modified exendin-4 was observed to have the most effective long-acting drug property.

Experimental Example 4-3

Pharmacokinetic Behavior

The same procedure as in Experimental Example 3-3 was repeated, with the exception that bi-branched PEG conjugates (20 kDa) and tri-branched PEG conjugates (23 kDa) prepared according to Example 3 were intravenously injected. The results are shown in Table 2 and FIG. 15.

TABLE 2

|  | PEG23k-Exendin-4 (tri-branched) | PEG20k-Exendin-4 (bi-branched) |
| --- | --- | --- |
| AUC(ng hr/ml) | 7659 ± 1365* | 5717 ± 1015* |
| Elimination Half Life(hr) | 25.1 ± 9.1 | 28.0 ± 10.4 |
| Volume of Distribution(ml) | 9.41 ± 1.57* | 25.45 ± 16.84 |
| Volume of distribution(L/kg) | 0.05 ± 0.01* | 0.13 ± 0.08 |
| Elimination rate (ml/hr) | 0.54 ± 0.09* | 0.63 ± 0.08* |
| Elimination rate(ml/hr/kg) | 2.69 ± 0.45* | 3.16 ± 0.39* |

As can be seen in the data of Table 2, the exendin-4, modified with tri-branched PEG, exhibited lower elimination rates than did the exedin-4 modified by bi-branched PEG. A far lower volume of distribution was detected in the exendin-4 modified with tri-branched PEG than with bi-branched PEG, indicating that the tri-branched PEG modified exendin-4 can exist most stably in the blood. In addition, although there is no significant difference in elimination half life between the exendin-4 modified with two kinds of PEG, the exendin-4 modified with tri-branched PEG exhibited the lowest elimination rate and the highest stability.

Figure 15:
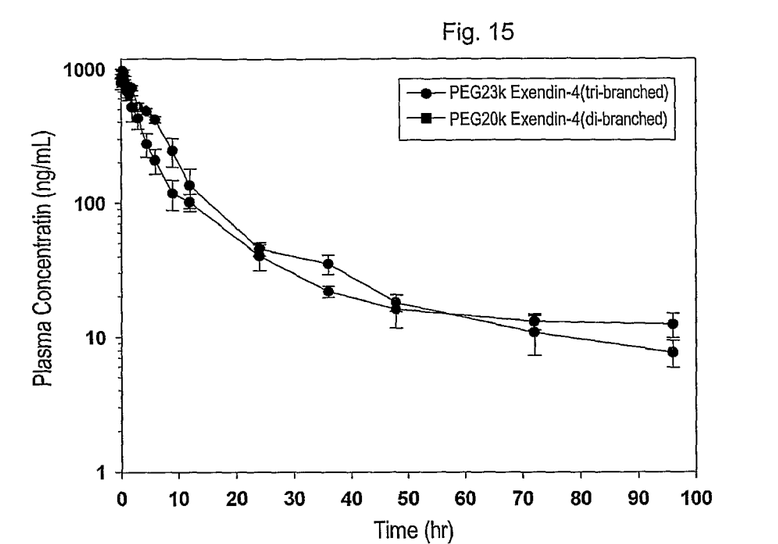
FIG. 15 shows pharmacokinetic behaviors of the exendin-4 singly modified with 20 kDa PEG of different molecular structures.

As can be seen in FIG. 15, the bi- or tri-branched PEG modified exendin-4 prepared according to Example 3 gradually decreased in blood level over a long period of time, but at different rates depending on the structure of PEG.

Experimental Example 4-4

Assay for Promoting Insulin Secretion

The same procedure as in Experimental Example 2-1 was repeated, with the exception that the cells were treated with 0.1, 1, 10 and 100 nM of natural exendin-4 or tri-branched PEG modified exendin-4. The results are shown in FIG. 16.

Figure 16:
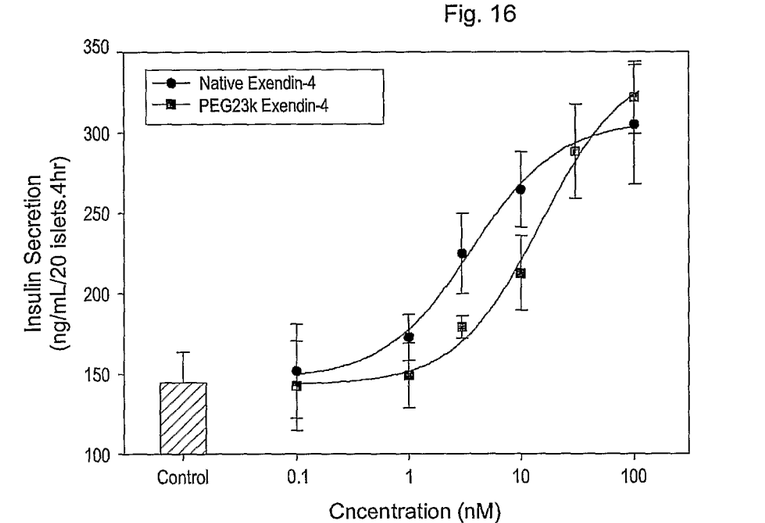
FIG. 16 shows the dose-dependent insulin secretory capacity of natural exendin-4 and the exendin-4 modified with 23 kDa tri-branched PEG.

As can be seen in FIG. 16, both natural exendin-4 and tri-branched PEG modified exendin-4 promote insulin secretion in a dose-dependent manner.

Experimental Example 5

Analysis of Exendin-4, Modified Singly at Lysine-27, with PEG for Biological Activity According to Molecular Weight of PEG Experimental Example 5-1

Measurement of Anti-Diabetic Activity in Animal

The same procedure as in Experimental Example 3-3 was repeated, with the exception that the cells were treated with 23 or 43 kDa tri-branched PEG-modified exendin-4 (PEG23k-Ex-4 or PEG43k-Ex-4). The results are shown in FIG. 17.

Figure 17:
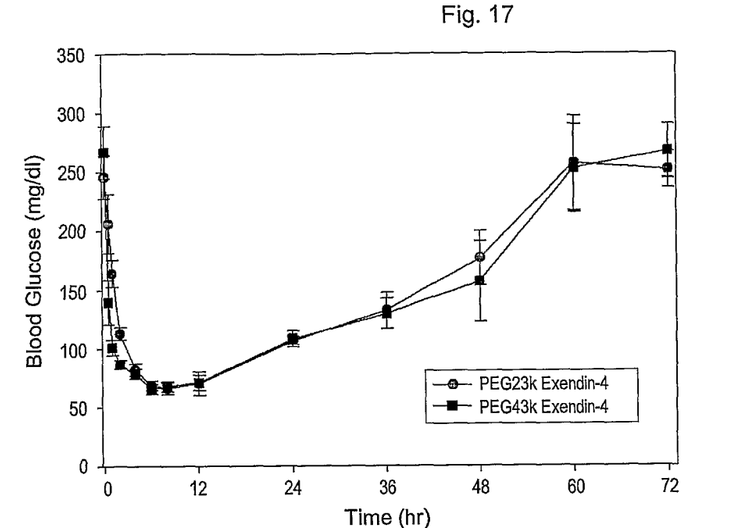
FIG. 17 shows measurements of anti-diabetic activity in animals administered with exendin-4 modified at lysine-27 with tri-branched PEG having various molecular weights.

As can be seen in FIG. 17, the molecular weight difference between 23 and 43 kDa PEG did not have any influence on the long-acting property of the modified exendin-4. In fact, both of the modified exendin-4s exhibited similar long-acting properties. Accordingly, the data demonstrate that tri-branched PEG having a molecular weight of 20 kDa or higher guarantees medicinal efficacy over a long period of time.

Experimental Example 5-2

Measurement of Exendin-4 Modified at Lysine-27 with Tri-Branched PEG for Anti-Diabetic Activity According to Dose The same procedure as in Example 3-3 was repeated, with the exception that the cells were treated with 23 kDa tri-branched PEG modified exendin-4 (PEG23k-Ex-4) at a dose of 10 nmol/kg or higher. The results are shown in FIG. 18.

Figure 18:
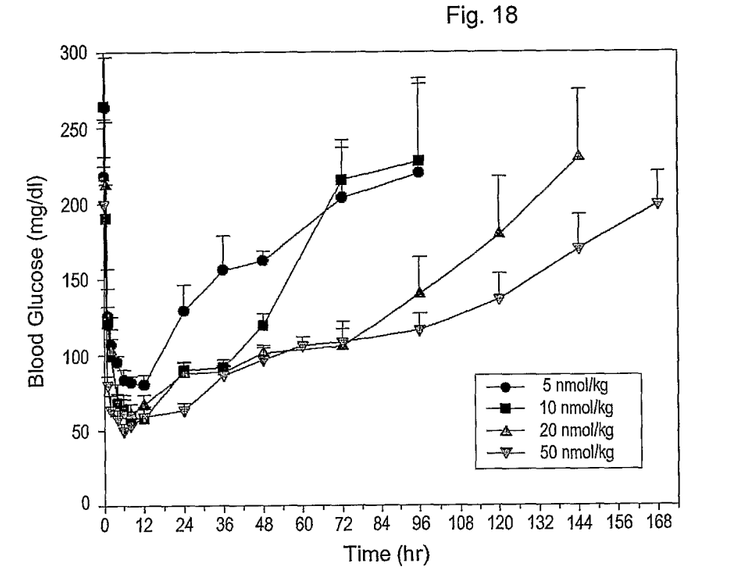
FIG. 18 shows measurements of anti-diabetic activity in animals administered with various doses of exendin-4 modified at lysine-27 with tri-branched PEG.

As can be seen in FIG. 18, the medicinal efficacy of the modified exendin-4 was observed to last for about 12-18 hours at a dose of 5 nmol/kg for about 36-48 hours at a dose of 10 nmol/kg and for about 72-96 hours at a dose of 20 nmol/kg. When administered at a dose of 50 nmol/kg the modified exendin-4 showed useful medicinal effects for periods as long as 120 hours.

Below, a description will be given of formulation examples of the composition according to the invention.

Formulation Example

Preparation of Pharmaceutical Formulations

Pharmaceutical formulations comprising the exendin-4 modified singly with PEG were prepared as follows.
1. Preparation of Powder
Exendin-4 singly modified with PEG 2 g
Lactose 1 g
These ingredients were admixed and loaded into an airtight sac to prepare a powder form.
2. Preparation of Tablet
Exendin-4 singly modified with PEG 100 mg
Corn starch 100 mg
Lactose 100 mg
Magnesium stearate 2 mg
These ingredients were admixed and tabletted according to a typical method to produce tablets.
3. Preparation of Capsule
Exendin-4 singly modified with PEG 100 mg
Corn starch 100 mg
Lactose 100 mg
Magnesium stearate 2 mg
These ingredients were admixed and loaded into gelatin capsules according to a typical method to produce capsules.

4. Preparation of Injection
Exendin-4 singly modified with PEG 10 μg/ml
Diluted HCl BP until pH 3.5
NaCl for injection BP up to 1 ml The exendin-4 singly modified with PEG was dissolved in a suitable volume of injectable NaCl BP and adjusted to pH 3.5 with diluted HCl BP. The volume was also adjusted with injectable NaCl BP, followed by sufficiently mixing the ingredients. The solution was loaded into 5 ml type I glass ampules which were then melted to seal them.

The invention claimed is:

1. An isolated exendin modified with polyethylene glycol or a polyethylene glycol derivative, wherein a single amino acid of said exendin is modified with polyethylene glycol or a polyethylene glycol derivative and wherein the polyethylene glycol or the polyethylene glycol derivative is a tribranched type.

2. The exendin according to claim 1, wherein the polyethylene glycol or the polyethylene glycol derivative ranges in molecular weight from 20 to 45 kDa.

3. The exendin according to claim 1, wherein the polyethylene glycol derivative is a tribranched polyethylene glycol derivative represented by the following chemical formula 1:

<Chemical Formula 1>

(wherein n is an integer of 1 to 1,000, m is an integer of 10 to 1,000, the N-hydroxysuccinimide moiety is a functional group able to chemically react with proteins and peptides including exendins, and Z is $(CH_2)_s$ or $(CH_2)_s NHCO(CH_2)_s$, serving as a linker between exendin and polyethylene glycol, wherein s is an integer of 1 to 6).

4. The exendin according to claim 1, wherein the polyethylene glycol or the polyethylene glycol derivative ranges in molecular weight from 23 to 43 kDa.

5. A composition comprising as an active ingredient the exendin modified with polyethylene glycol or a polyethylene glycol derivative of claim 1.

6. A method for preparing the exendin modified with polyethylene glycol or a polyethylene glycol derivative of claim 1, comprising:
reacting polyethylene glycol or a derivative thereof with exendin in the presence of a reducing agent in a solvent (step 1);
storing the reaction mixture of step 1 at a predetermined temperature for a predetermined period of time in the dark (step 2);
removing unreacted materials from the reaction mixture (step 3); and separating and purifying the exendin modified with polyethylene glycol or its derivative from the reaction mixture free of unreacted materials (step 4).

7. The method according to claim 6, wherein the solvent used in step 1 is phosphate buffer saline or an organic solvent.

8. The method according to claim 7, wherein the organic solvent is dimethyl sulfoxide DMSO.

9. The method according to claim 6, wherein the reaction molar ratio of the polyethylene glycol or polyethylene glycol derivative thereof to exendin is within the range of 1:1-4.

* * * * *

UNITED STATES PATENT AND TRADEMARK OFFICE
CERTIFICATE OF CORRECTION

PATENT NO.       : 8,420,598 B2
APPLICATION NO.  : 12/596010
DATED            : April 16, 2013
INVENTOR(S)      : Lee et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 219 days.

Signed and Sealed this
First Day of September, 2015

Michelle K. Lee
*Director of the United States Patent and Trademark Office*